United States Patent [19]
Yu et al.

[11] Patent Number: 5,985,893
[45] Date of Patent: Nov. 16, 1999

[54] PHYSICALLY STABLE SOLID FORM OF A FLUOROQUINOLONE

[75] Inventors: Xuanqiang Yu; William C. Schinzer, both of Portage; Michael J. Dunn, Paw Paw; Robert Shih-Liang Chao, Portage; Dale S. Aldrich, Richland; Azhwarsamy Jeganathan; Michael S. Bergren, both of Portage, all of Mich.

[73] Assignee: Pharmacia & Upjohn Company, Kalamazoo, Mich.

[21] Appl. No.: 08/641,569

[22] Filed: May 1, 1996

Related U.S. Application Data

[63] Continuation of application No. 08/342,202, Nov. 18, 1994, abandoned.

[51] Int. Cl.[6] .................. A61K 31/47; C07D 215/56
[52] U.S. Cl. .............................. 514/312; 546/156
[58] Field of Search .................. 514/312; 546/156

[56] References Cited

U.S. PATENT DOCUMENTS

| | | | |
|---|---|---|---|
| 4,521,431 | 6/1985 | Crooks | 514/471 |
| 5,563,155 | 10/1996 | Domagala | 514/312 |

FOREIGN PATENT DOCUMENTS

| | | |
|---|---|---|
| 1242582 | 8/1989 | Japan . |
| 2006099 | 4/1989 | Spain . |
| WO 92 09596 | 6/1992 | WIPO . |
| 93/15070 | 8/1993 | WIPO . |

OTHER PUBLICATIONS

B. Sustar, N. Bukovec, and P. Bukovec, J. Therm. Anal. 40, 475–481 (1993).

Katdare, A.V.; J.A. Ryan; J. F. Bavitz, et al. Mikrochim Acta, (1986) vol. 3(1–2), pp. 1–12.

J. M. Domagala et al., *Journal of medicinal chemistry,* 36, 7, pp. 871–882 (1993).

Domagala JM, Hagen SE, Joannides T, Kiely JS, Laborde E, Schroeder MC, Sesnie JA, Shapiro MA, Suto MJ, Vanderroest S. (1993) J. Med. Chem. 36, 871–882.

*Primary Examiner*—C. Warren Ivy
*Assistant Examiner*—Evelyn Huang
*Attorney, Agent, or Firm*—Thomas A. Wootton

[57] ABSTRACT

Novel crystal forms of the fluoroquinolone, [S-(R*,S*)]-1-cyclopropyl-6-fluoro-1,4-dihydro-8-methoxy-7-[3-[1-(methylamino)ethyl]-1-pyrrolidinyl]-4-oxo-3-quinolinecarboxylic acid are disclosed. The forms are characterized by one methanol solvate form, and three anhydrous polymorphic forms, of which, Form III exhibits greatest stability and decreased hygroscopicity.

8 Claims, 11 Drawing Sheets

PHYSICALLY STABLE SOLID FORM OF A FLUOROQUINOLONE

The present patent application is a continuation application of U.S. patent application Ser. No. 08/342,202, filed Nov. 18, 1994 abandoned.

FIELD OF THE INVENTION

This invention relates to the field of antibiotic quinolones, in particular, a novel crystal form of a fluoroquinolone named, [S-(R*,S*)]-1-cyclopropyl-6-fluoro-1,4-dihydro-8-methoxy-7-[3-[1-(methylamino)ethyl]-1-pyrrolidinyl]-4-oxo-3-quinolinecarboxylic acid.

INFORMATION DISCLOSURE

WO93/15070 (Chugai) A novel crystalline form of a quinolone. This form is considered to be "stable against moisture."

J01242582 (Hokuriku) A novel crystalline form of a quinolone.

ES2006099 (Investchemi) The preparation of a dihydrate of the quinolone antibiotic ciprofloxacin.

B. Sustar, N. Bukovec, and P. Bukovec, J. Therm. Anal. 40, 475–481 (1993). "Polymorphism and Stability of Norfloxain, 1-Ethyl-6-fluoro-1,4-dihydro-4-oxo-7-(1-piperazinil)-3-quinolinocarboxylic acid". A study on the finding of a more stable polymorph of a structural analog to norfloxacin.

Katdare, A. V.; J. A. Ryan; J. F. Bavitz, et al. Mikrochim. Acta, (1986) Vol. 3(1–2), pp. 1–12. "Characterization of hydrates of norfloxacin." Three hydrated forms of norfloxacin are discussed, the dihydrate has the greatest thermodynamic stability at room temperature.

U.S. Pat. No. 4,521,431, issued on Jun. 4, 1985, discloses forms 1 and 2 of ranitidine hydrochloride.

BACKGROUND OF THE INVENTION

Quinolone type structures are known for their antibacterial properties, and several quinolone antibiotics (e.g. norfloxacin and ciprofloxacin) are on the market. The physical properties of a marketed quinolone are very important. A quinolone with excellent antibiotic properties but which has a shelf life of only a day would be useless. A quinolone with excellent antibiotic properties but which does not dissolve into a useful solvent would be equally useless. Quinolones, when purified, may form crystals or crystal like forms, that can have different shapes and physical properties.

Solids, including pharmaceuticals, often have more than one crystal form and this is known as polymorphism. Polymorphism occurs when a compound crystallizes in a multiplicity of solid phases that differ in crystal packing. Numerous examples are cited in the standard references of solid state properties of pharmaceuticals, Byrn, S. R., Solid-State Chemistry of Drugs, New York, Academic Press (1982); Kuhnert-Brandstatter, M., Thermomiscroscopy In The Analysis of Pharmaceuticals, New York, Pergamon Press (1971) and *J. Pharm. Sci.,* 58, 911 (1969). Byrn states that, in general, polymorphs exhibit different physical characteristics including solubility and physical and chemical stability.

Because of differences in molecular packing, polymorphs may differ in ways that influence drug release, solid-state stability, and pharmaceutical manufacturing. The relative stability and the interconversions of polymorphs are particularly important to the selection of a marketed drug. A suitable polymorph may hinge upon the issue of physical stability. For example, the selection of a marketed drug may depend upon the availability and selection or a suitable polymorph having desirable characteristics, such as excellent physical stability. The performance of the solid dosage form should not be limited by polymorphic transformations during the shelf life of the product. It is important to note that there is no reliable method to predict the observable crystal structures of a given drug or to predict the existence of polymorphs with desirable physical properties.

This invention describes a new form of a quinolone that has physical properties highly desirable for pharmaceutical development.

SUMMARY OF THE INVENTION

Figure 4:
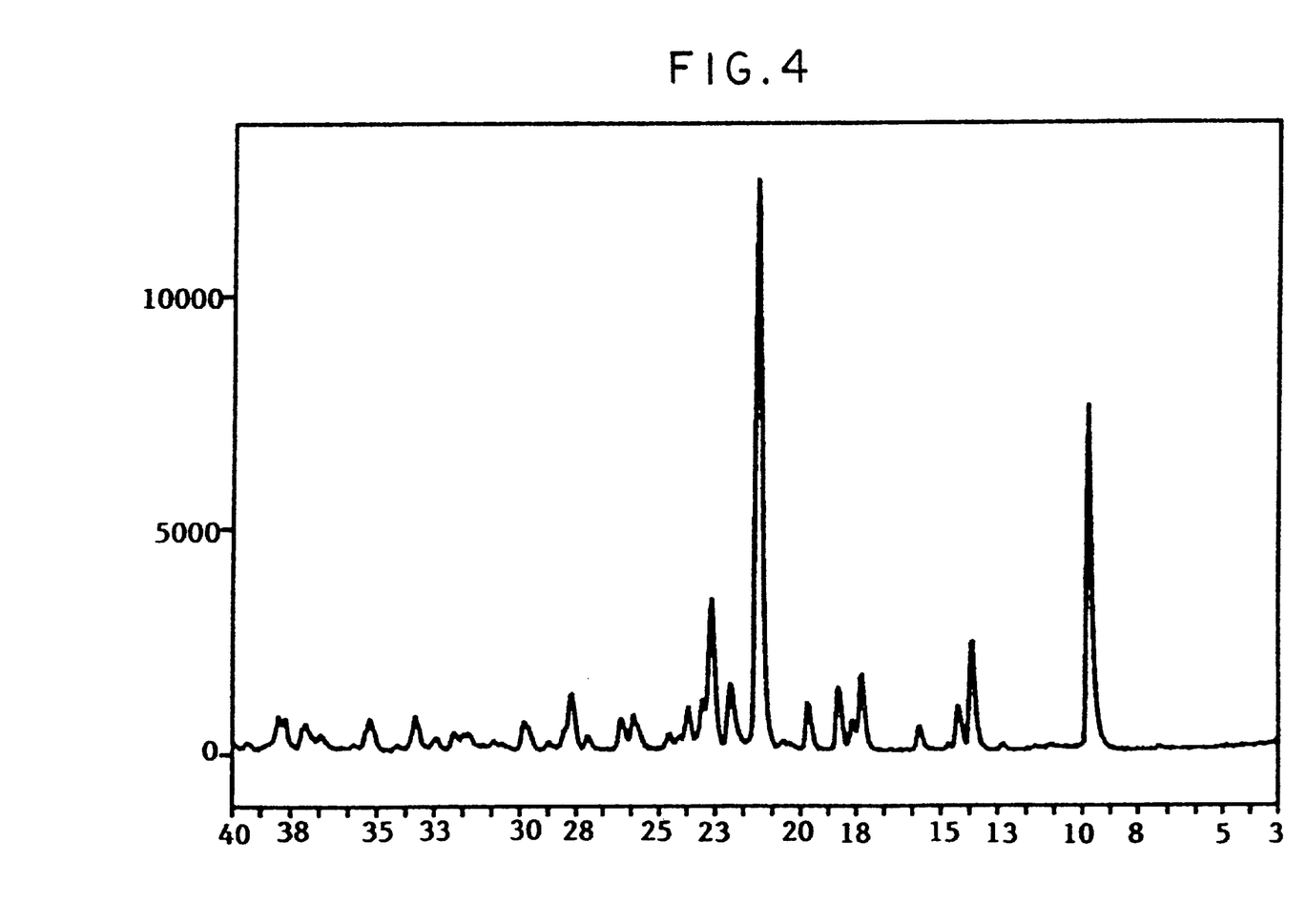
FIG. 4. The X-ray diffraction (XRD) powder pattern of Form III.
Figure 5:
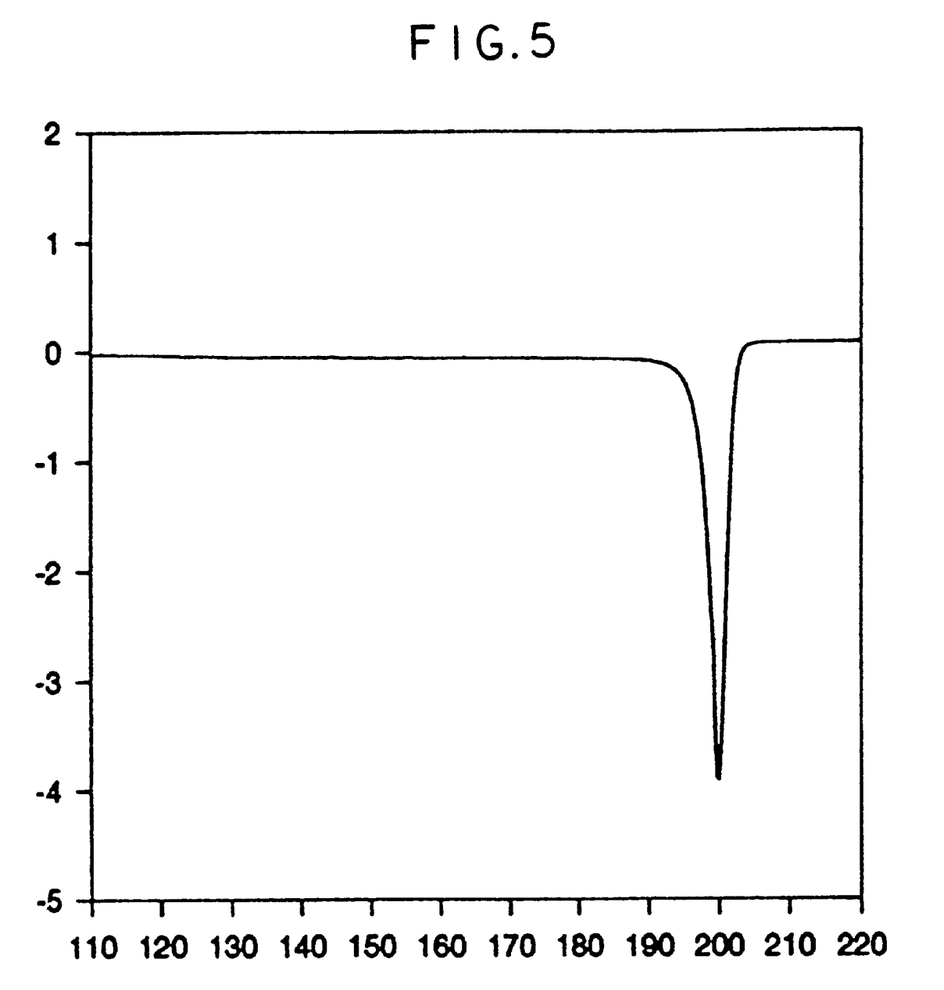
FIG. 5. The DSC profile of the quinolone, Form III.

This invention comprises a compound comprising the crystal form of [S-(R*,S*)]-1-cyclopropyl-6-fluoro-1,4-dihydro-8-methoxy-7-[3-[1-(methylamino)ethyl]-1-pyrrolidinyl]-4-oxo-3-quinolinecarboxylic acid, referred to as "the quinolone," having the formula shown below, and having a melting onset range, as determined by Differential Scanning Calorimetry (DSC) between 190–202° C., or between 195–201° C., or between 198–201° C., depending on purity, or as shown in FIG. 5, or having the X-Ray Diffraction pattern described by TABLE III, or having the X-Ray Diffraction pattern shown in FIG. 4. The invention also comprises a pharmaceutical composition which comprises this same the crystal form of the quinolone.

ADDITIONAL DESCRIPTION OF THE INVENTION

Definitions and Methods

Various standard methods are described. The definitions and explanations below are for the terms as used throughout this entire document including both the specification and the claims.

Optical Microscopy

The drug is examined with a Wild M5 stereomicroscope, from 6× through 50× magnification. Drug samples are mounted dry or in a variety of selected liquid media, such as mineral oil, silicone oil, Cargille MeltMount and water. Particle size, habit and crystallinity are examined with a Nikon Optiphot polarized light microscope or an Olympus BHSP polarized light microscope from 40× through 600× magnification.

Thermomicroscopy

A Nikon POH-2 polarized light compound microscope with 10× objective is employed to view specimens mounted dry between a glass microscope slide and a no. 1½ Cover slip. The samples are heated from ambient through 250° C. in a Mettler FP-80 microfurnace controlled by a Mettler FP-8 microprocessor. The heating rates may vary from 5–20° C./minute. The hot-stage experiments may be videotaped (Sony T120-HG and PM VHS tape) with a Hitachi VK-C350 Color Video Camera and a Panasonic AG-6200 Video Cassette Recorder.

Powder X-Ray Diffraction (XRD)

A Rigaku DMAX-A X-ray diffractometer is employed for the acquisition of the powder XRD patterns. The instrument is operated with the copper K-$L_3$ radiation at 1.5406 Å. The major instrumental parameters are set as follows: 40 KV voltage, 30 mA current, beam aperture of 1° and detector aperture (receiving slit) of 0.30°. Patterns are scanned over the range of 3–40° two-theta angles with a scan rate of 1.5° two-theta/min (step size of 0.05° and counting time at 2 second/step). Samples are ground to fine powders and packed into an aluminum tray.

Differential Scanning Calorimetry

Differential scanning calorimetry (DSC) is used to monitor enthalpy changes as a function of temperature during a linear temperature increase. A DuPont 910 DSC interfaced to a TA Instruments TA2100 computer may be used. The scan rate is 5° C./minute, and the instrument is operated with a 50–80 cc/min dry nitrogen purge. Samples are encapsulated in hermetically sealed aluminum sample pans with a pressure rating of about 2 bar. In some experiments, the lids of the pans are perforated to permit the passage of moisture and other volatile components.

Because calorimetric samples are occasionally affected by residual moisture, samples are sometimes studied with different initial water activities. Samples are weighed into tared DSC pans, and the open pans are permitted to equilibrate for several days in chambers of constant relative humidity at 25±1° C. These chambers are prepared from saturated salt solutions at 53% RH and 75% RH. At the end of the equilibration period, the chambers are opened, and the lids are placed over the samples to prevent re-equilibration with the ambient atmosphere. The samples are removed from the chambers, and the pans are quickly crimped closed.

Dynamic Moisture Sorption Gravimetry

Dynamic moisture uptake is studied on the controlled atmosphere microbalance system at 25° C. About ten mg of sample are equilibrated on the balance for about 2 hours at 2.5% RH. The relative humidity surrounding the sample is increased in increments of 3% RH up to about 92% RH, at which point the RH is decremented in 3% steps to a final RH of about 2.5%. At each relative humidity, the sample is allowed to equilibrate until the mass is stable within 0.0005 mg over a ten minute period. The dry mass is assumed to correspond to the mass of the sample after the initial equilibration period. A controlled atmosphere microbalance is a balance system described by Bergren, M.S. Int. J. Pharm. (1994) Vol. 103, pp. 103–114.

Microhygrostat

A small glass container having a volume of approximately 0.5 ml, within which is a saturated salt solution. If the salt is sodium chloride, for example, the relative humidity inside the container will be maintained at 75%. When a microhygrostat is placed inside another container, the salt will dissolve or crystallize such that the humidity inside the larger container will equilibrate to that of the microhygrostat.

HPLC Assay Conditions

A Hewlett-Packard 1090 liquid chromatograph equipped with a ChemStation controller is used to assess chemical purity. The separation of the target compound from related compounds is accomplished using a YMC ODS-AQ 3 micron packing in a 4.6×100 mm column at ambient temperature. The mobile phase consists of 75% (100 mM phosphoric acid, 46 mM tetrabutylammonium hydroxide at pH 3): 25% (methanol, tetrahydrofuran, acetonitrile in volume ratios 837/93/70). The mobile phase is pumped at a rate of 0.7 ml/min. Detection is accomplished by monitoring UV absorbance at 298 nm. The injection volume is 10 $\mu$l.

Bulk drug samples are prepared by dissolving the material in mobile phase at a final concentration of approximately 0.25 to 0.5 mg/ml. For solubility experiments, 100 mcl aliquots of ethyl acetate solutions are withdrawn and placed directly into HPLC autosampler vials. A gentle stream of nitrogen gas is used to evaporate the solvent in the sample vials. The solids are reconstituted with 0.5 ml of HPLC mobile phase prior to analysis.

Solubility

Solubilities are measured in ethyl acetate. Five to ten milligrams of bulk drug are placed into an amber autoinjector vial, and 3.0 ml of ethyl acetate are added. The vials are capped and shaken for intervals up to 24 hours at room temperature using a Burrell model BB wrist-action shaker. Aliquots are withdrawn from the supernate after centrifugation. The final sample is taken from a quiescent solution which had not been shaken since the 24 hour timepoint.

Isothermal Calorimetry

Isothermal calorimetry (ITC) experiments are conducted using a model 2277 microcalorimeter made by ThermoMetric (see Suurkuusk, J.:Wadso, I. Chem. Scr. (1982) Vol. 20 pp. 155–163). The Digitam® version 2.1 software from Thermometric is used to display the data and to integrate the total heat obtained from the samples. Heat flow is monitored as a function of time at 60° C. and at 40° C. Both glass and stainless steel ampules are used to hold the solid samples and the reference material (quartz sand). Samples are thermally equilibrated for a period ranging from 15 minutes (glass ampules) to 1 hour (stainless steel ampules) prior to recording thermal data. The weight of the samples ranged from about 75 to 300 mg. Samples in glass ampules are equilibrated via the isopiestic method at 53% or 75% RH in chambers containing saturated solutions of sodium chloride or calcium nitrate tetrahydrate. The ampules are capped immediately after removing the samples. Other samples are equilibrated using "microhygrostats" containing small quantities of saturated salt solutions which are sealed within the ampules. This arrangement provided for nearly constant relative humidity as the crystal conversion proceeded.

Enthalpies of Solution

The enthalpies of solution are determined in 50 mL of 0.1 M HCl at 25.0±0.05° C. Samples (0.10–0.11 g) are weighed in 2 ml spherical, soft glass ampules and dried overnight in an evacuated desiccator over $P_2O_5$. The ampules are removed, capped, weighed, and flame sealed. The enthalpies of solution are measured on a Tronac model 458 isoperibol solution calorimeter. The calorimetric accuracy of this instrument is within 1% based on calibration with tris (hydroxymethyl)-aminomethane (TRIS) in 0.1 N HCl.

Further standard terms and definitions when not provided are understood to be what is commonly accepted by those skilled in the art.

All temperatures are in degrees Centigrade. RH is Relative Humidity. HPLC is High Pressure Liquid Chromatography. When solvent pairs are used, the ratios of solvents used are volume/volume (v/v). When the solubility of a solid in a solvent is used the ratio of the solid to the solvent is weight/volume (wt/v).

COMPOUNDS OF THE INVENTION

[S-(R*,S*)]-1-cyclopropyl-6-fluoro-1,4-dihydro-8-methoxy-7-[3-[1-(methylamino)ethyl]-1-pyrrolidinyl]-4-oxo-3-quinolinecarboxylic acid is a member of the quinolone family of antibiotics. Its molecular structure, is shown by either of the formulas below, (stereochemical orientation is indicated)

For the purposes of this document the compound represented by the formulas above will simply be referred to as, "the quinolone compound." Studies on the quinolone compound have revealed three anhydrous polymorphic forms, Form I, II and III, as well as a methanol solvate form, Form MS. Only one form, Form III, is stable to transformation, the other two anhydrous forms, Forms I and II, and the methanol solvate form, Form MS, undergo phase transformations under a variety of conditions.

Preparation of Form III

The form III material can be prepared by dissolving the quinolone in hot methanol and slowly distillatively methanol with a nonpolar solvent having a higher boiling point. The quinolone should be only sparingly soluble in the solvent displacing methanol. The various solvents that can be used for this purpose are ethyl acetate, butyl acetate, toluene, heptane etc. In one example, Form III is obtained by dissolving 2.7 g of Form I in 50 ml of hot methanol and clarifying by filtration through a glass funnel. The clear yellow solution is distilled to remove about 25 ml of methanol and 50 ml of ethyl acetate are added slowly during the continued distillation of methanol. After distilling off another 40 ml of solvent, another 50 ml of ethyl acetate are added and distillation continued until the pot temperature rises to 74° C. The off-white precipitate is filtered hot on a glass funnel, washed with 2×25 ml of ethyl acetate, and dried in a vacuum oven to afford 2.0 g of Form III.

The Methanol Solvate, also known as Form MS, also known as the methanolate

The most stable form, Form III, cannot be crystallized directly from methanol. We inferred the existence of a methanol solvate when we failed to crystallize the most stable form, Form III, from methanol. The methanol solvate form is produced when the quinolone compound is isolated using methanol as the solvent in the crystallization step. After taking care to avoid desolvation, we isolated the methanol solvate. The methanol solvate is prepared by dissolving the quinolone compound in methanol (200 mg of the quinolone, Form I, in about 8 ml of methanol works well) and then sealing the suspension in a glass vial and heating over a steam bath to achieve complete dissolution. The sample is allowed to cool overnight and crystals are collected by vacuum filtration the following morning.

The methanol solvate form, Form MS, or the methanolate, has a subtle influence on the appearance and characteristics of Form I. The methanolate forms readily and makes it impossible to grow the stable anhydrate, Form III, in methanol. The methanolate desolvates to yield Form I under such mild conditions that solvent is not normally retained in the product crystals. The methanolate is discovered only after it is learned that Form III cannot be grown from methanol. Form I is thus obtained via a relatively simple synthetic isolation procedure, yet it is the product of a solid-state desolvation process that yields a hygroscopic polymorph susceptible to physical transformation.

Another method of isolation is to use ethyl acetate as the solvent in the crystallization step. Using ethyl acetate in the final reaction step produces Form III, no solvate is produced when ethyl acetate is used. The Form III solid produced possesses a unique combination of greater stability and decreased hygroscopicity; we thus produce a surprising, very useful and unexpected type of crystal quinolone that has never before been created or described.

Forms I, II, and III

If Form I is slowly heated, under the proper conditions, it produces Form II, at the temperature range of 140–151° C., which, with further heating under the proper conditions, produces Form III at the melt/recrystallization range of 166–171° C. Microscopically, Form II appears to convert via growth from seed crystals present in the original Form I sample.

In samples of Form I where the initial water activity is at least 53% RH, direct conversion of Form I to Form III occurs without the formation of Form II. The conversion is observed at temperatures as low as 40° C. in the microcalorimeter. The rate of conversion increases dramatically for samples initially equilibrated at 75% RH at room temperature. These samples convert completely to Form III in less than one day at 60° C.

Dry samples of Form I convert to Forms II and III through a sequence of melts and recrystallizations. It is possible to transform the quinolone compound directly from Form I into Form III without any appearance of the Form II. Sealed, humidified samples of Form I transform directly to Form III via a moisture-meditated solid-state process. Form III is stable to transformation, but the other two forms, Form I and II, undergo phase transformations under a variety of conditions. Form III is the preferred form for pharmaceutical preparations.

Form III can be isolated as a solid directly via recrystallization from hot ethyl acetate. Form III material thus produced is not contaminated with the other solid phases. Form III is recommended for pharmaceutical preparations because it is the most stable form of the quinolone compound found to date, and it is less hygroscopic than Form I. Form I is an energetic, low melting polymorph relative to the more stable crystal Form III. Form III, grown directly from solution is lower in Gibbs free energy by about 7.7 kJ/mole and lower in enthalpy by about 8.8 kJ/mole than Form I. The difference in hygroscopicity of the two forms is dramatic. Above 80% RH, Form I adsorbs sufficient moisture to irreversibly transform to an apparent monohydrate, while Form III adsorbs less than 0.5% moisture throughout the entire RH range. Form III is more stable than Form I, but it is also less soluble than Form I. Form I is about 20 times more soluble than Form III in ethyl acetate at room temperature.

CHARACTERIZATIONS OF THE VARIOUS FORMS

Form I

Form I is isolated as an off-white, fine powder. Microscopically, the material is crystalline (that is, it exhibits one or more of the following properties: regular interfacial angles, cleavage planes, or birefringence), but the particles are asymmetric and occur in clumped and layered aggregates of lath to needle-shaped solids. Larger aggregates appear dark in transmitted illumination, due to the light scatter caused by misaligned crystals and multiple layers. Typically, incomplete, parallel extinction is observed in crossed polarized light. Two refractive indices are measured: $n_{min}$=1.563 and $n_{max}$=1.591.

The purity of one sample of the Form I material is 99.2%, based on analysis of minor components including water, drug-related impurities (HPLC), and residue on ignition. The total HPLC impurities are determined with the method described in the HPLC assay description. A value of 0.20% by area is obtained when a relative response factor of 1.0 for the individual impurities is assumed.

Figure 1:
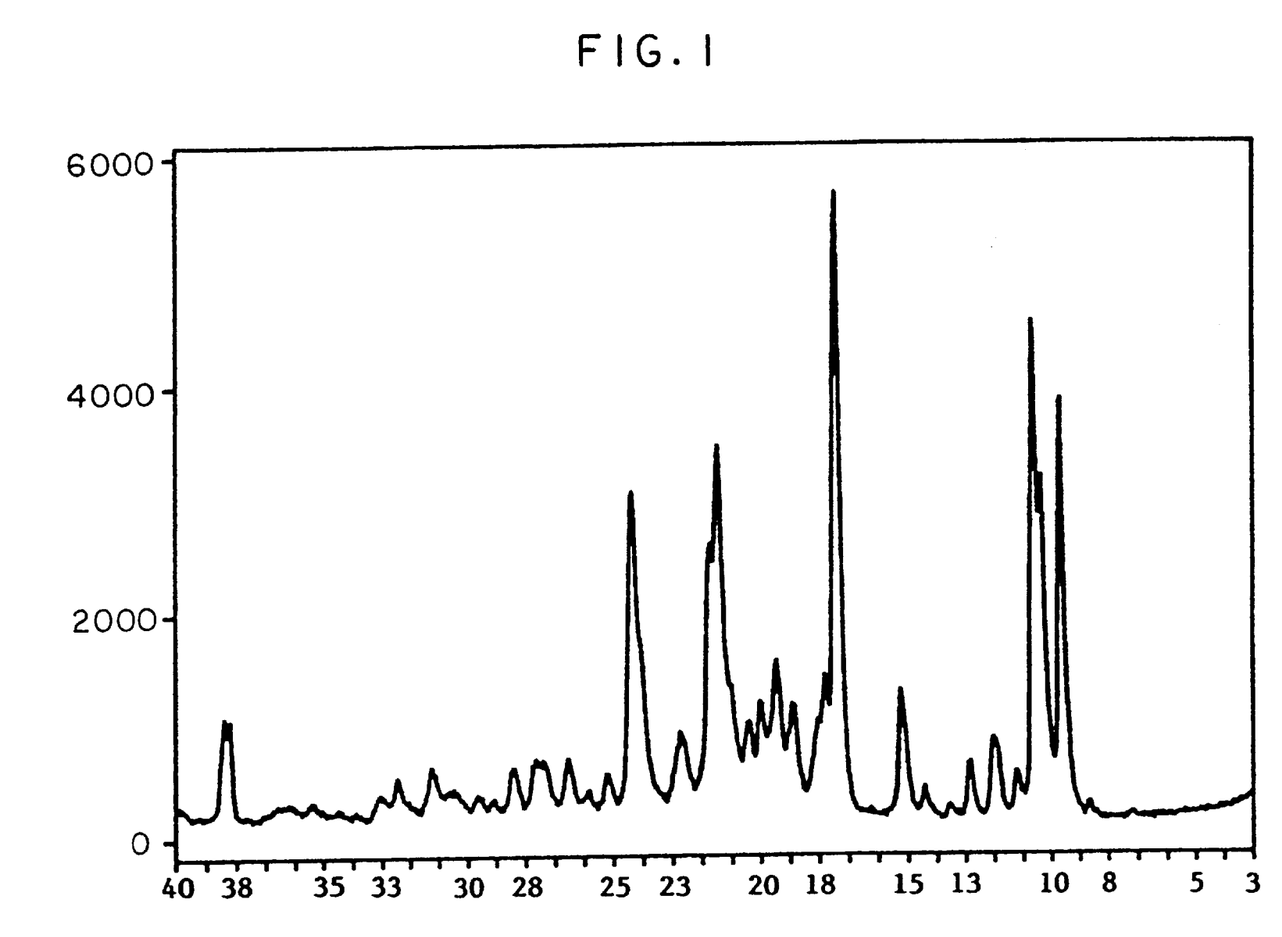
FIG. 1. The X-ray diffraction (XRD) powder pattern of Form I.

The X-ray diffraction (XRD) powder pattern of Form I is shown in FIG. 1. The narrow peaks and low background of the diffraction profile indicate that the material is highly crystalline. The diffraction pattern does not change after Form I is exposed to 75% relative humidity at ambient temperature for 5 days.

Figure 2:
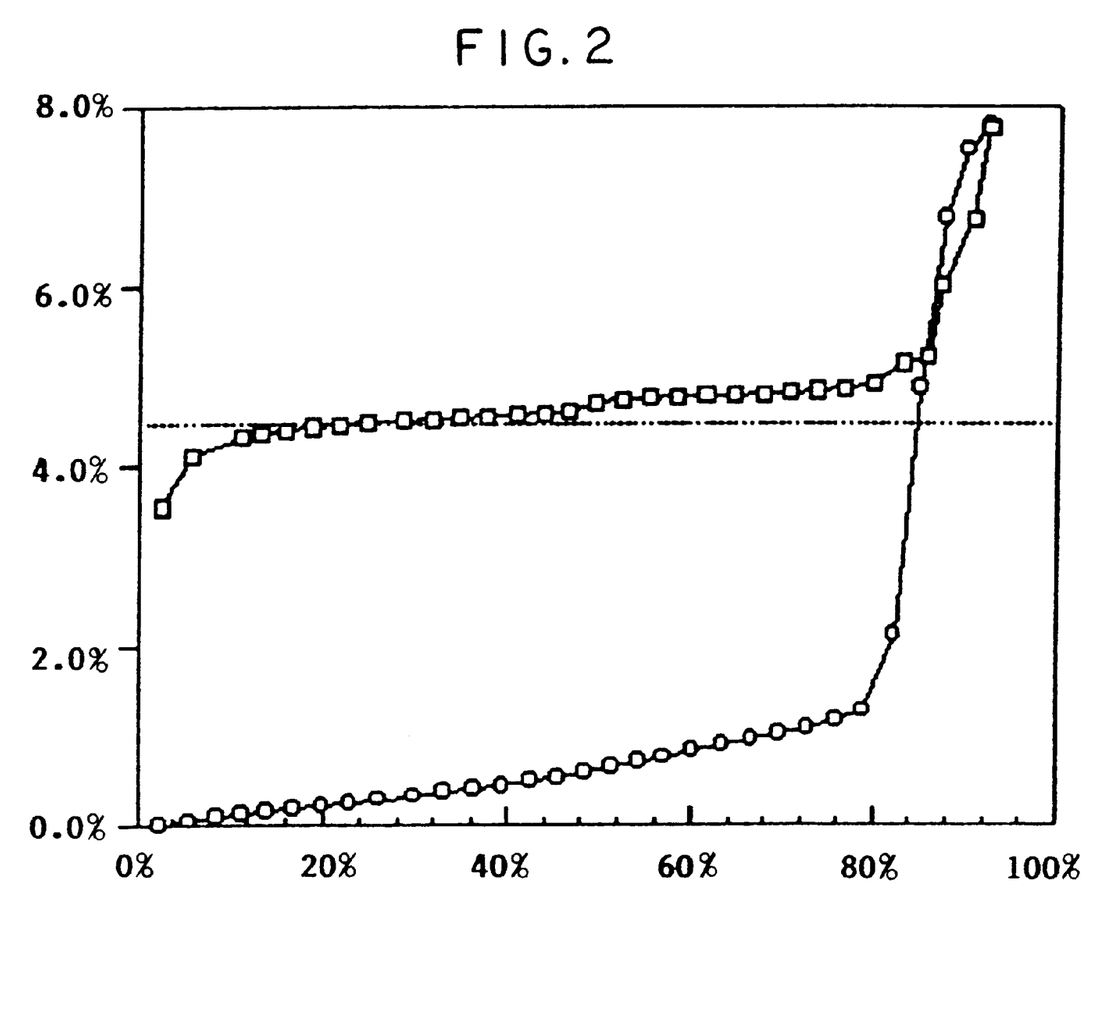
FIG. 2. Moisture sorption of the quinolone, Form I, by gravimetric measurements in a controlled atmosphere.

The moisture sorption profile of Form I is shown in FIG. 2. The sample is moderately hygroscopic at ambient relative humidity: moisture pickup is 1% up to 70% RH. Just above 80% RH, moisture sorption increased significantly. The moisture in the sample reached a plateau of about 7.5–7.7% w/w at 90–92% RH. As the RH is decreased, the moisture content dropped to about 4.9% at 80% RH. The moisture content decreased gradually at intermediate RHs to about 4.3% at 10% RH. The stable moisture plateau on the desorption profile is close to the water content of the ideal monohydrate—4.46%.

Detailed description of FIG. 2. FIG. 2 shows the moisture sorption of the quinolone, Form I, by gravimetric measurements in a controlled atmosphere. The ordinate represents the mass change relative to the lowest mass measurement. The abscissa is relative humidity. The circles represent points recorded after sequential increases in the relative humidity and the squares were recorded after decreases in the relative humidity. The horizontal line in the middle of the plot corresponds to the water content of the hypothetical monohydrate of the quinolone.

Form II

Figure 3:
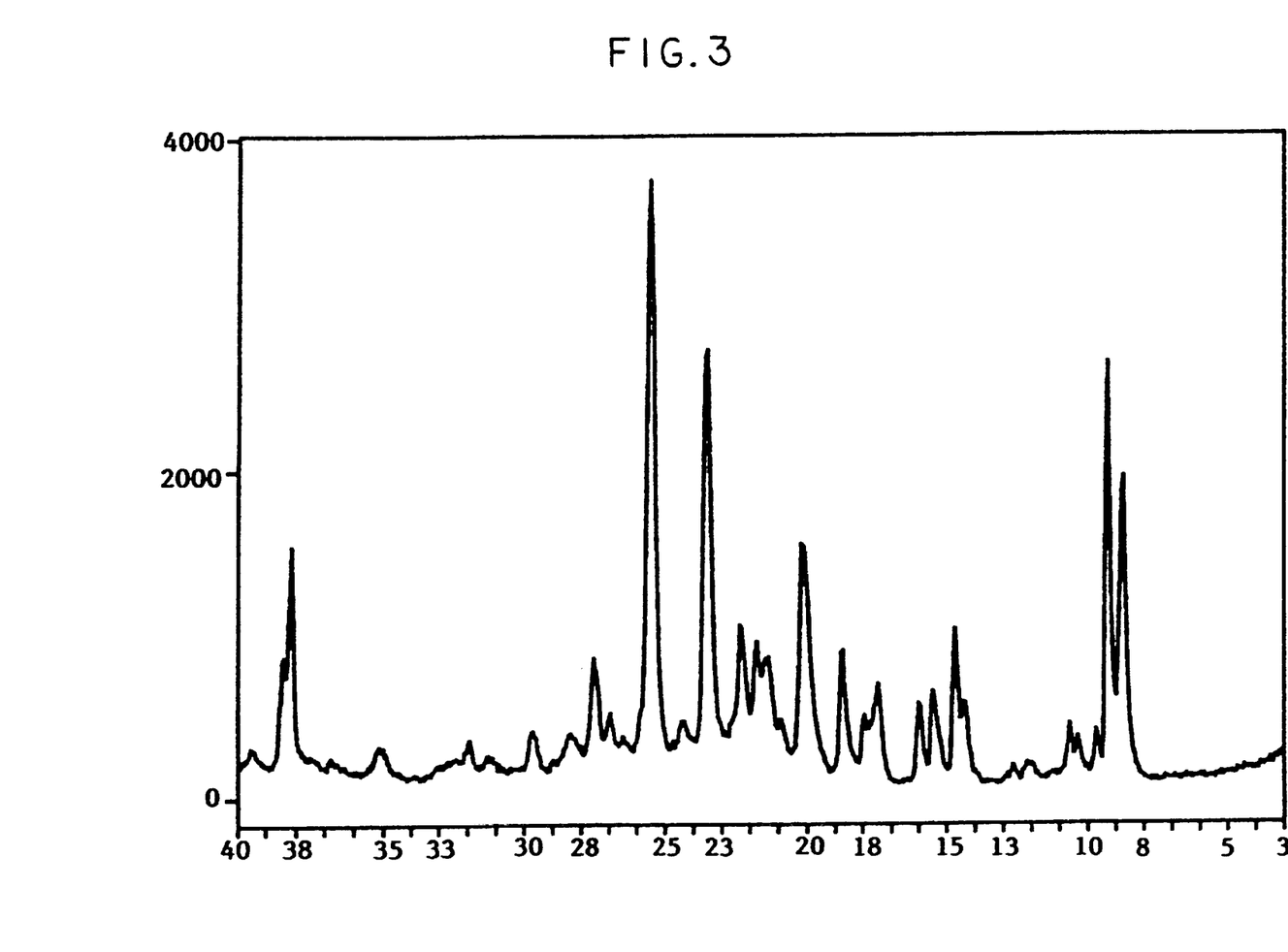
FIG. 3. The X-ray diffraction (XRD) powder pattern of Form II.

To obtain Form II for X-ray analysis, we heated a sample of Form I to 150° C. at 5° C./minute in a TGA furnace. The resultant material is moderately crystalline with a distinct XRD pattern shown in FIG. 3. The XRD profile of the heated material consists of Form II features with a minor features at 2θ angles near 17.4 and 10 ascribed to Form I.

Form III

The form III material can be prepared by dissolving the quinolone in hot methanol and slowly distillatively displacing methanol with a nonpolar solvent having a higher boiling point. The quinolone should be only sparingly soluble in the solvent displacing methanol. The various solvents that can be used for this purpose are ethyl acetate, butyl acetate, toluene, heptane etc. In one example, Form III is obtained by dissolving 2.7 g of Form I in 50 ml of hot methanol and clarifying by filtration through a glass funnel. The clear yellow solution is distilled to remove about 25 ml of methanol and 50 ml of ethyl acetate are added slowly during the continued distillation of methanol. After distilling off another 40 ml of solvent, another 50 ml of ethyl acetate are added and distillation continued until the pot temperature rises to 74° C. The off-white precipitate is filtered hot on a glass funnel, washed with 2×25 ml of ethyl acetate, and dried in a vacuum oven to afford 2.0 g of Form III.

Form III crystals grown from ethyl acetate, as described above, appeared as an off-white powder. The HPLC potency is 98.2% for this material, relative to the Form I material employed as a standard. TGA showed that little volatile matter (including about 0.1% water by KF) is present in the Form III samples; less than 0.3% mass loss is observed up to the melting point (data not shown).

Microscopical examination revealed crystalline laths and elongated plates in small sizes generally below 20 μm. Larger aggregates are also present. Complete, parallel extinction is observed in crossed polarized light. Three principal refractive indices are measured, $n_\alpha$=1.527, $n_\beta$=1.70, and $n_\gamma$=1.8. The birefringence is therefore≈0.27.

XRD and DSC confirmed the distinctive character of this sample and established the absence of measurable quantities of the other phases. The powder pattern shown in FIG. 4 reflects the highly crystalline nature of the sample. Peaks characteristic of Forms I and II are absent. The DSC profile of Form III is shown in FIG. 5. Due to instrumental differences and changes in sample purity the melting point onset may shift to values within the range of 190–202° C. If the compound is reasonably pure the range is expected to be between 195–201° C. Generally speaking, impurities depress the melting point below the normal melting range. The melt for this particular sample of Form III was observed at an onset temperature of 198.7° C. The enthalpy of fusion is approximately 150 J/g. The absence of transitions at lower temperatures confirmed the absence of Forms I and II and other potential forms.

Detailed description of FIG. 5. The DSC profile of the quinolone, Form III. The ordinate is heat flow in units of watts/gram and the abscissa is temperature in units of ° C. The heating rate is 5° C./minute.

Figure 6:
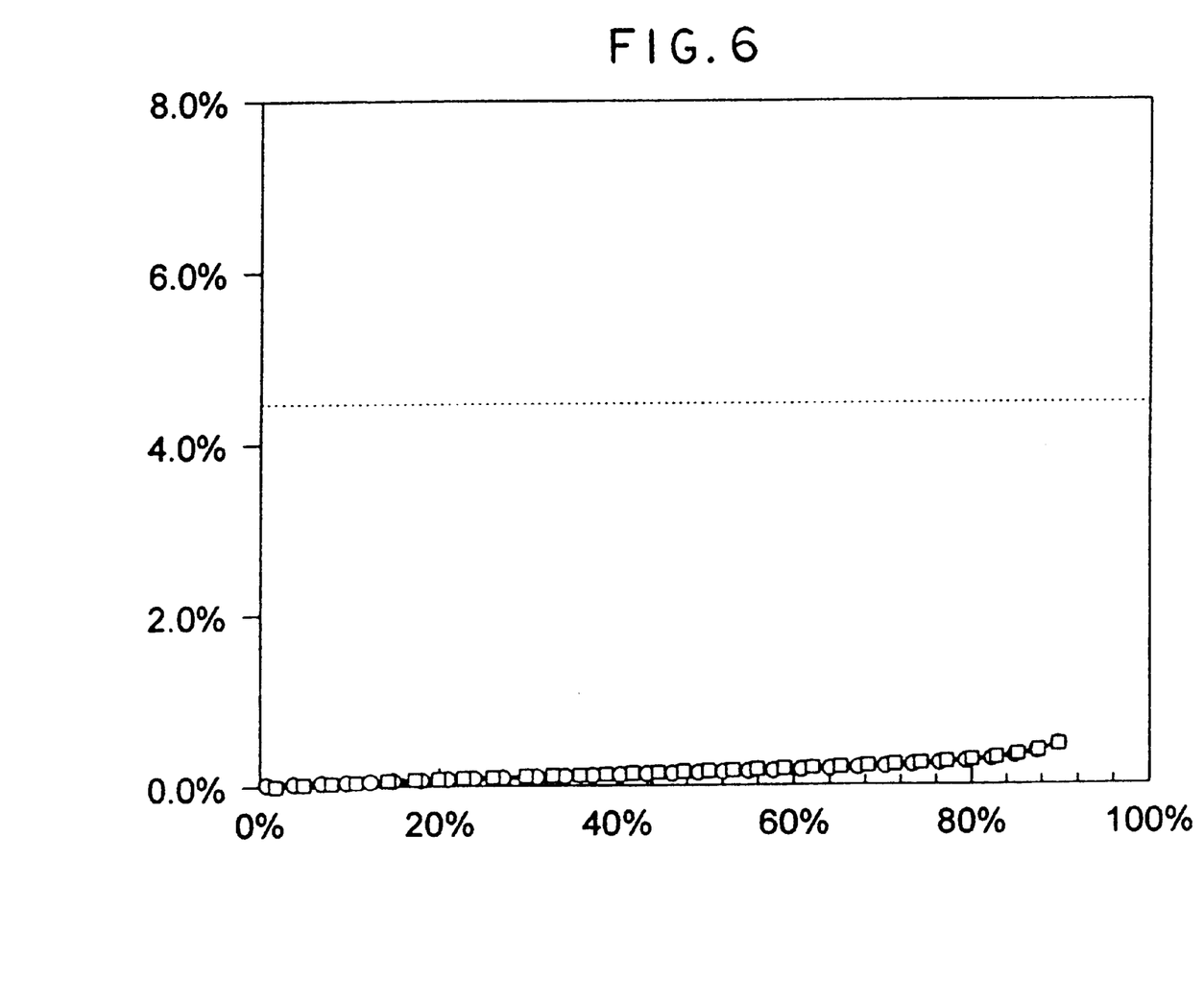
FIG. 6. Moisture sorption of the quinolone, Form III, by gravimetric measurements in a controlled atmosphere.

Form III sorbs less moisture than Form I at all relative humidities. The equilibrium moisture sorption profile for Form III is shown in FIG. 6. There is very little hysteresis between the sorption and desorption profiles, and the sample exhibited no evidence of recrystallization and/or hydrate Formation.

Detailed description of FIG. 6. FIG. 6 shows the moisture sorption of the quinolone, Form III, by gravimetric measurements in a controlled atmosphere. The ordinate represents the mass change relative to the lowest mass measurement. The abscissa is relative humidity. The circles represent points recorded after sequential increases in the relative humidity and the squares were recorded after decreases in the relative humidity. The horizontal line in the middle of the plot corresponds to the water content of the hypothetical monohydrate of the quinolone.

The Methanol Solvate

Figure 7:
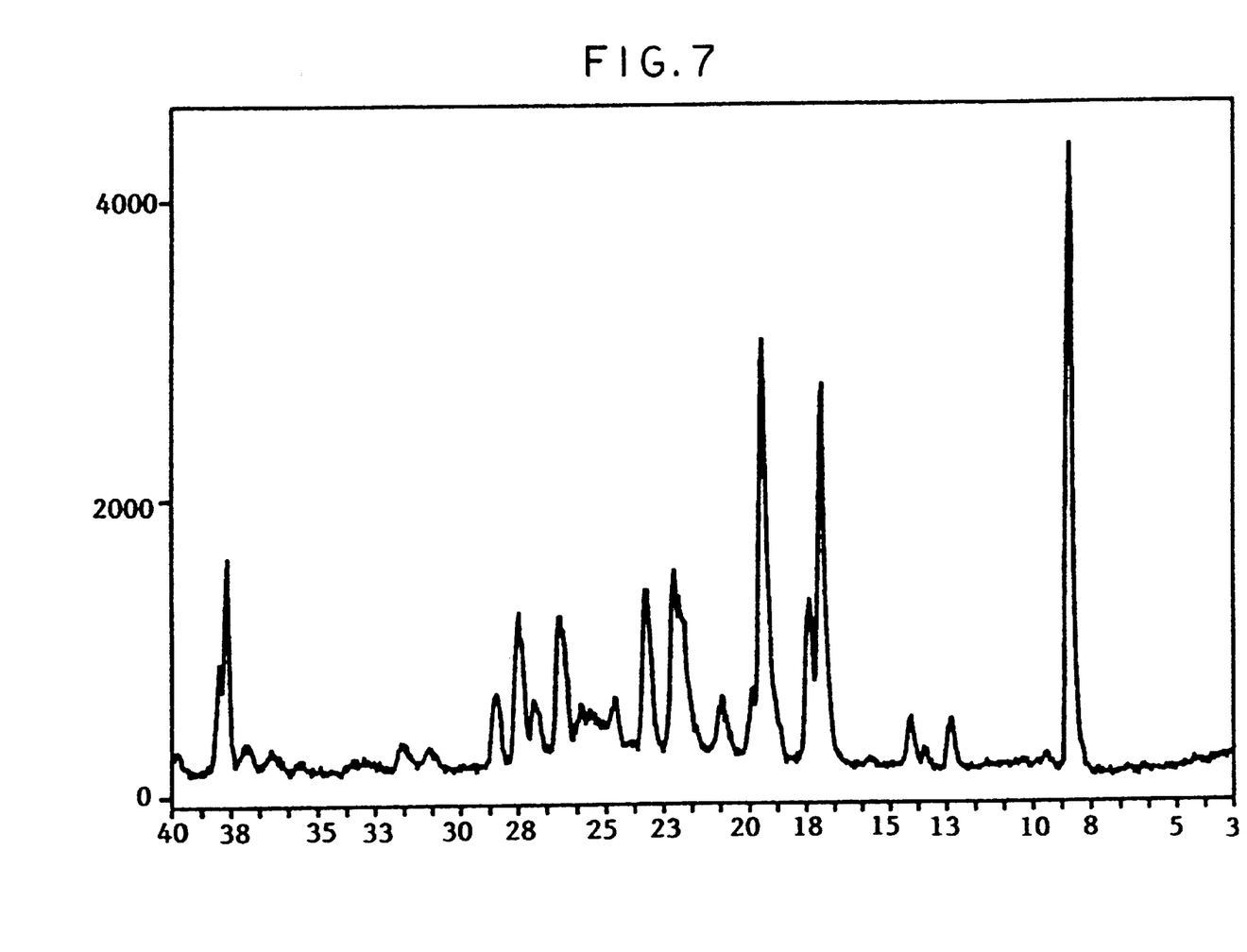
FIG. 7. The unique XRD powder pattern of the methanol solvate.

The unique XRD powder pattern of this sample is shown in the top frame of FIG. 7. This methanol solvate may be desolvated by heating at 70° C. under vacuum for 5 hours to yield Form I. The Y axis of FIG. 7 is intensity and the X axis is the two theta angle.

Transitions of the Various Forms

Figure 8:
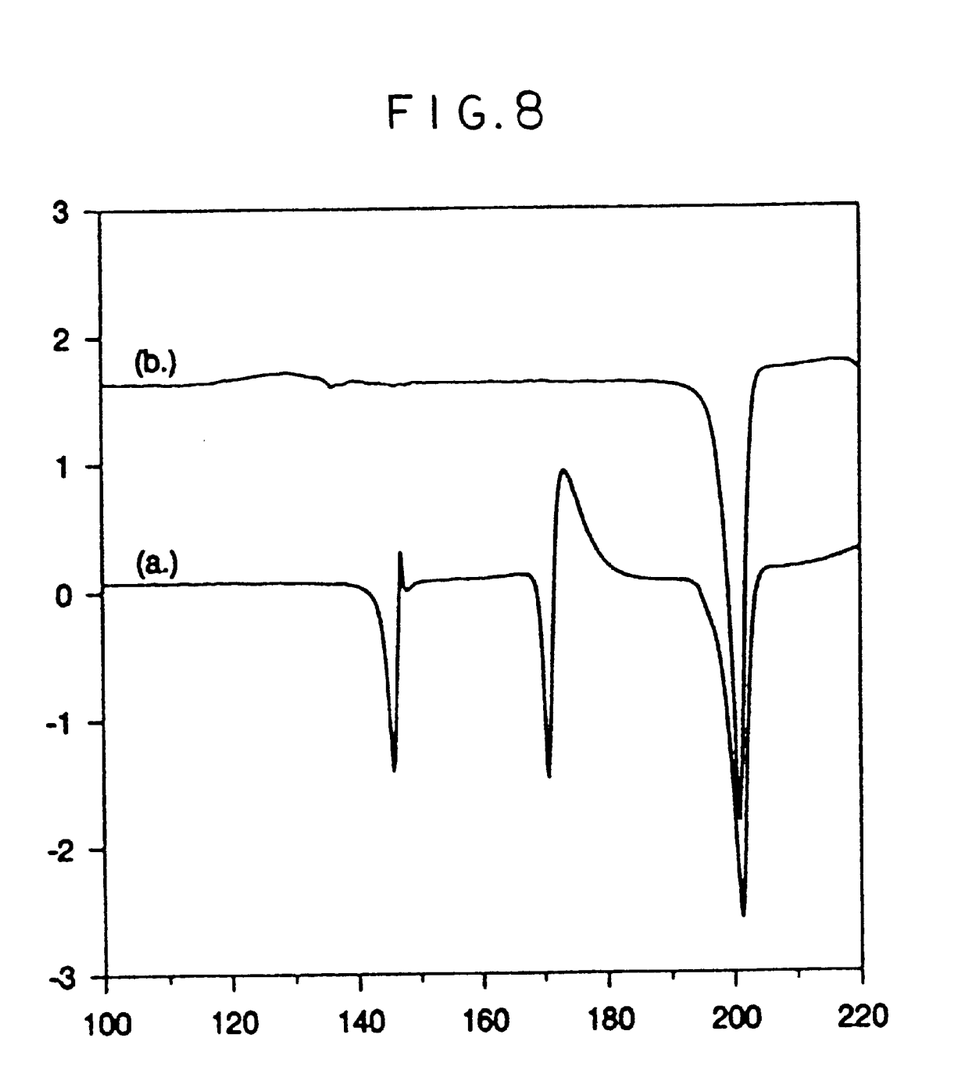
FIG. 8. DSC profiles of the quinolone, Form I.

Thermomicroscopy and DSC uncovered a sequence of thermal transformations starting from Form I and proceeding through two additional solid phase transitions prior to the final melt. The DSC profile of Form I is shown in FIG. 8. The merged endotherms and exotherms at 140–150° C. and at 165–180° C. represent combined melt/recrystallizatioN events. The final melt endotherm at 200° C. is followed by a broad exothermic decomposition of the melt. These assignments are confirmed by thermomicroscopic observations of Form I at heating rates of 5 and 10° C./minute. The crystal Form designations are based upon the sequence of thermomicroscopic transformations. The melt/recrystallization at 143–151° C. is assigned to the Form I→Form II transformation, and the second melt/recrystallization from 166–171° C. is assigned to the Form II→Form III transformation. Form III melting onset is between 190–202° C., the purer samples melting between 195–202, the more pure samples between, 195–201, the more purer samples between 198–201. Thermomicroscopy observations provided evidence that both Form II and Form III appeared to grow from seed crystals present in the Form I melt. Growth of Form II is relatively rapid compared to the growth of Form III.

Detailed description of FIG. 8. FIG. 8 shows the DSC profiles of the quinolone, Form I. The ordinate is heat flow in units of watts/gram and the abscissa is temperature in units of ° C. The heating rate is 5° C./minute. (a.) The sample is encapsulated in a standard DSC pan. (b.) The sample is encapsulated in a hermetically sealed DSC pan. The profiles are offset along the ordinate axis for comparison.

Figure 9A:
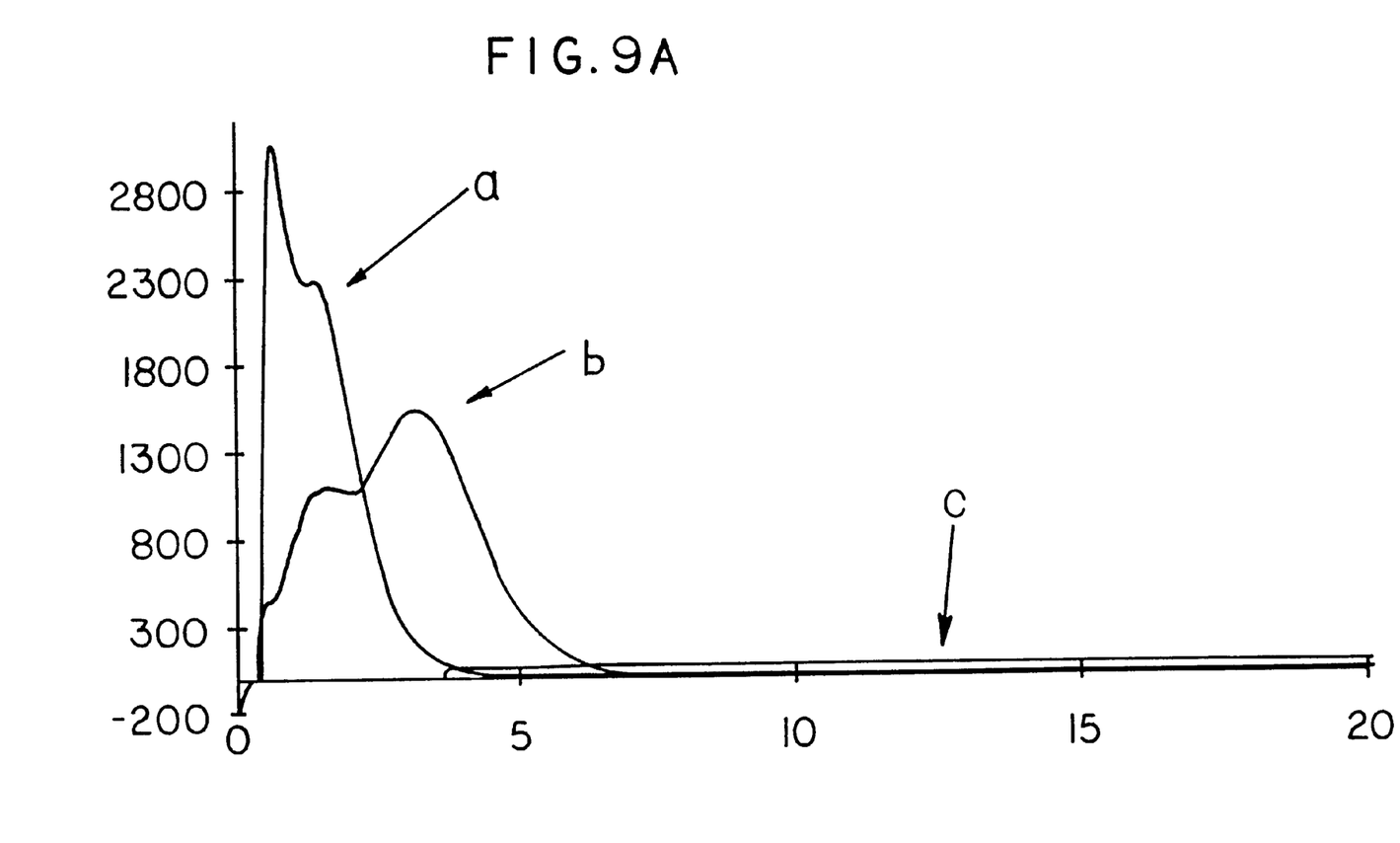
FIG. 9. Heat flow profiles for Forms I and III.
Figure 9B:
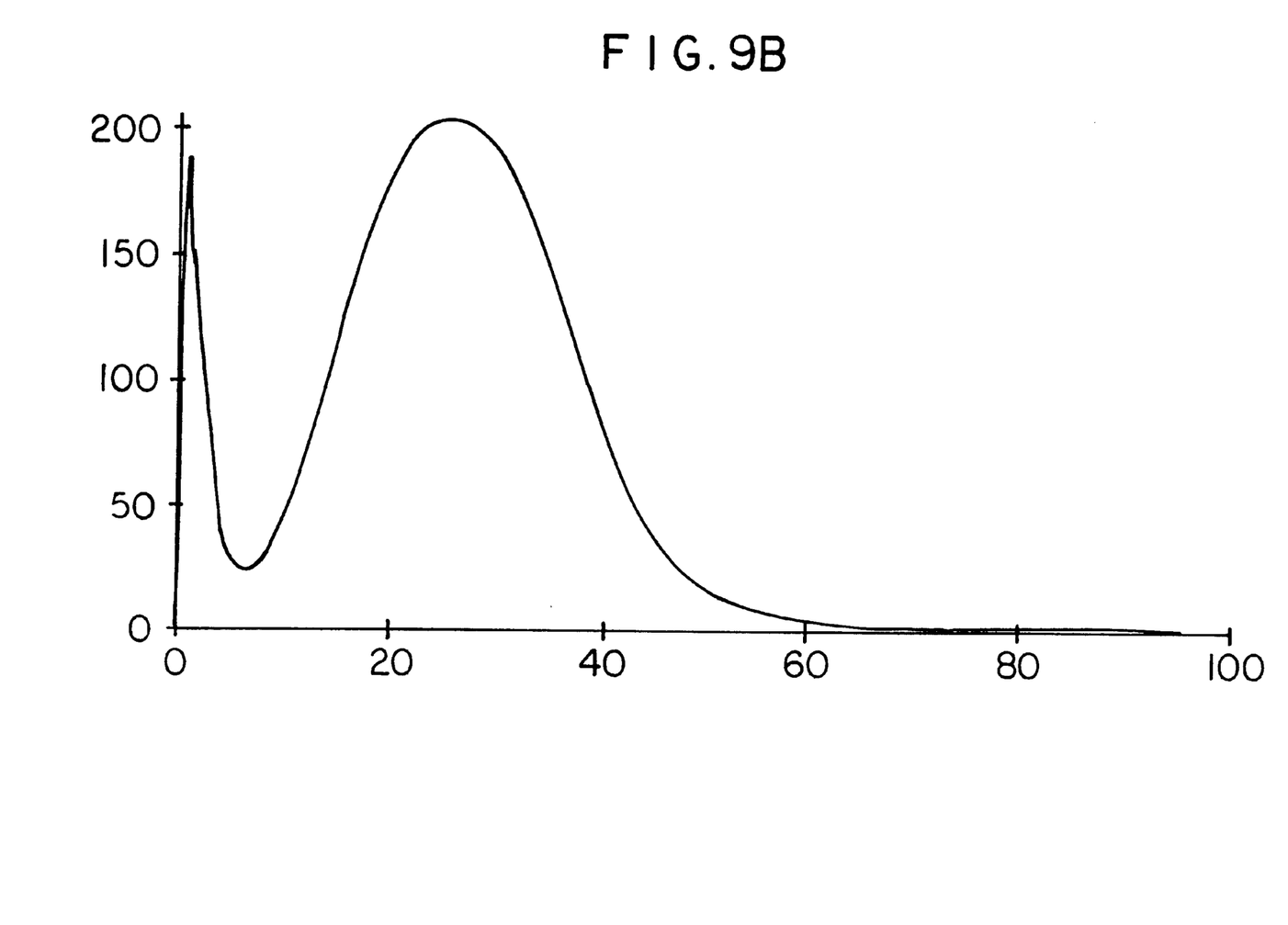

ITC revealed that Form I converted to Form III at temperatures as low as 40° C. Our early ITC results, obtained at 60° C., suggested that the rate of conversion at this temperature is sensitive to water. We therefore studied the transformation of samples after equilibration at 51% and 75% RH. The heat flow profiles for these samples are shown in FIG. 9(*a*). The rates of conversion from Form I to Form III differed significantly between these two samples; the rate is slower at 51% RH than at 75% RH by about two orders of magnitude. Both XRD and DSC confirmed that the high moisture sample had converted completely to Form III. HPLC analysis of the reaction product confirmed that the 60° C. ITC profiles contained negligible contributions from chemical decomposition.

The enthalpy change for the microcalorimetric transformation is obtained by integrating the heat flow over the time required for the sample to convert. The average of three results obtained at 60° C. is 18.3 J/g, or 7.4 kJ/mol. The low moisture sample shown in FIG. 9(*a*) had an integrated enthalpy change of about 10 J/g after 80 hours. XRD results confirmed that the sample is a mixture of Forms I and III.

The 40° C. data is shown in FIG. 9(*b*). The initial exothermic feature is likely due to sorption of moisture by the drug, decreased by both the heat of vaporization of moisture from the microhygrostat as well as crystallization of a small amount of NaCl. The broader exotherm beginning at about 6 hours and ending at about 50 hours is the sum of the heat of transition from Form I to Form III and the heat of desorption of water from the product crystals. Since the moisture content of the recovered Form III crystals is 0.61%, and the initial water content of the Form I sample is 0.54%, there is little heat exchanged in the overall profile due to moisture uptake and release. Thus, we integrated the entire profile shown in FIG. 9(*b*) to approximate the heat of crystal Form conversion. Our result is expressed as $\geq$20.4 J/g or $\geq$8.2 kJ/mol; the inequality is the result of our inability to integrate the initial heat flow profile as the sample equilibrated and our lack of knowledge of the initial concentration of Form II and Form III seed crystals.

A detailed explanation of FIG. 9 follows. Plot "(a)" shows heat flow on the y-axis in units of microwatts per gram as a function of time in hours on the x-axis. Trace (a) is recorded from a sample of Form I equilibrated to 75% relative humidity before sealing the sample container and exposing it to the 60° C. conditions in the calorimeter. Trace (b) is recorded for a sample of Form I at 60° C., but a 75% relative humidity "microhygrostat" is placed in the sample container just prior to recording the data. The conversion is delayed from that of trace (a) due to the fact that the water must be transported from the microhygrostat to the Form I crystals during the experiment. Trace (c) is recorded for a sample of Form I at 60° C., but the sample was equilibrated at 53% relative humidity prior to sealing the sample container.

Plot "(b)" shows heat flow on the y-axis in units of microwatts per gram as a function of time in hours on the x-axis. This trace results from placing a 75% relative humidity microhygrostat into the sample container just prior to recording the data. The sample is held at 40° C. in the calorimeter; the heat flow results as the Form I material converts to Form III.

Interestingly, we never observed Form II as a product of Form I transformation in the microcalorimeter. Apparently, the presence of sorbed moisture provided a direct low temperature route for the conversion to Form III without promoting the growth of Form II. Form I did not convert to Form III under dry conditions, even after greater than 7 days at 40° C./50% RH or after 5 days at 60° C.

Figure 10:
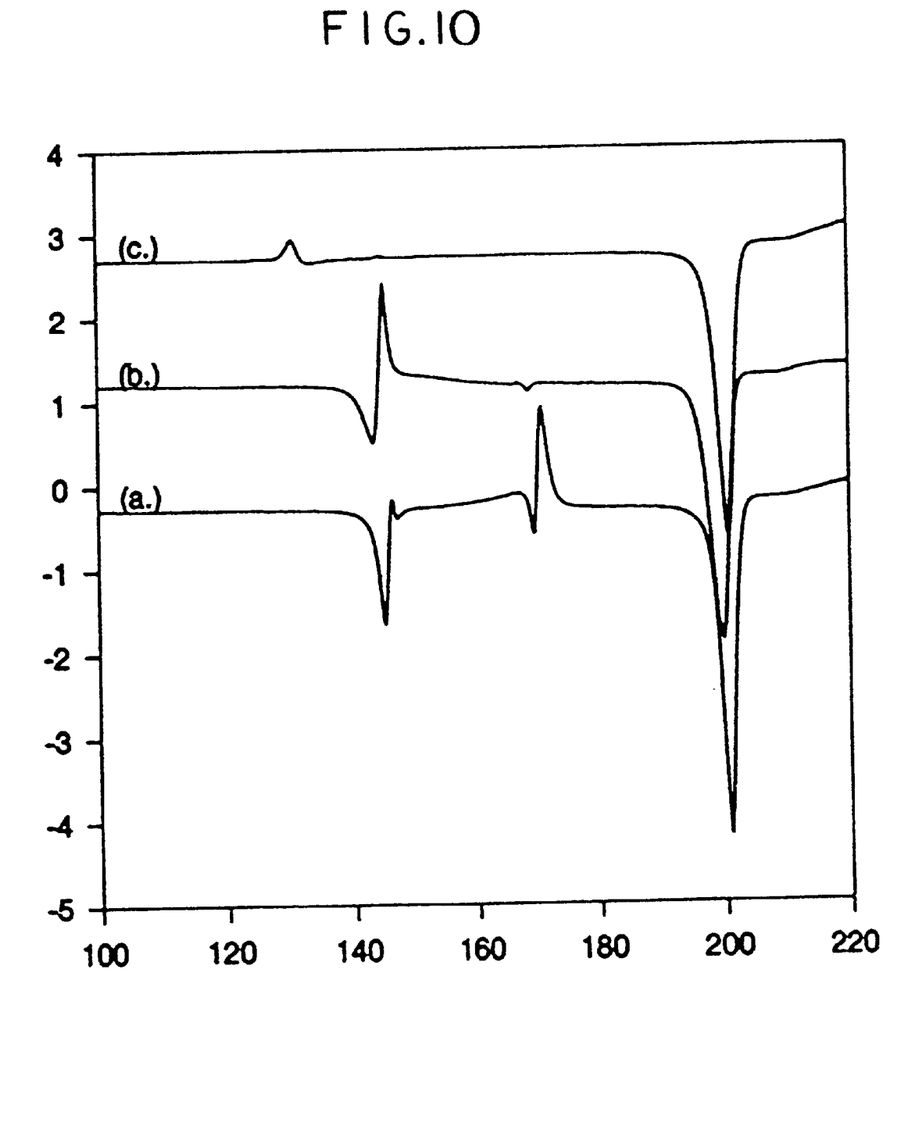
FIG. 10. DSC profiles of the quinolone, Form I.

That moisture influenced the conversion of phases is also illustrated by the results of three DSC scans in FIG. 10. Scan (a) represents the sample equilibrated at 53% RH and sealed in a perforated DSC pan. This scan shows a sequence of transitions comparable to those shown in FIG. 8. In contrast, scans (b) and (c) represent samples encapsulated in hermetically sealed DSC pans, where moisture is retained throughout the DSC scan. In scan (b), where the drug is equilibrated at 53% RH, the sample melted and recrystallized in the 140–150° C. range and finally melted as Form III at 200° C. Very little change is observed in the second transformation range from 165–175° C. Since scan (a) revealed that the conversion from Form II to Form III is exothermic, we conclude that the transformation at 140–150° C. is probably a direct transformation of Form I to Form III. When the drug is equilibrated at 75% RH [Scan (c)] the only visible transformation prior to the Form III melt is a small exotherm at about 130° C. We speculate that enough moisture is present in this sample to generate rapid conversion from Form I→Form III in the pre-melt region for Form I. The DSC trace provides no evidence that any Form II is formed in this sample.

Detailed description of FIG. 10. FIG. 10 shows DSC profiles of the quinolone, Form I. The ordinate is heat flow in units of watts/gram and the abscissa is temperature in units of ° C. The heating rate was 5° C./minute. (a.) The sample was equilibrated at 53% RH and encapsulated in a standard DSC pan. (b.)The sample was equilibrated at 53% RH and encapsulated in a hermetically sealed DSC pan. (c.) The sample was equilibrated at 75% RH and encapsulated in a hermetically sealed DSC pan. The profiles were offset along the ordinate axis for comparison.

The solubilities of Forms I and III were determined in ethyl acetate at room temperature; the solubility data for each form was gathered simultaneously, to assure that each form's solubility was measured under identical conditions. Ethyl acetate was employed as an aprotic solvent yielding fairly low equilibrium solubilities of the quinolone; ethyl acetate has been used to evaluate the difference in free energy of polymorphic forms of an antinociceptive drug, as described by K. Raghavan et al., *J. Pharm. Biomed. Anal.* Vol.12 (6), pp. 777–785 (1994). The results are given in TABLE S, below. Under the assumption that the solubilities in TABLE S are consistent with the dilute solution limit, we can use the following expression to calculate the difference in Gibbs free energy between Form I and Form III:

$$\Delta G_{I \to III} = -RT \ln \frac{s_I}{s_{III}} \quad (1)$$

where "$s_x$" is the solubility of Form x in a sufficiently dilute solution, R is the gas constant, and T is the absolute temperature. Using the data in Table 1, we find that the Gibbs free energy of Form III is lower than that of Form I by 7.7±0.2 kJ/mole.

The difference in solubilities is quite significant, the higher-energy Form I being greater than 20 times more soluble than the more stable Form III. This difference and the difference noted in hygroscopicity demonstrate that the two forms possess quite different properties. A particular advantage of form III in this regard is the predicted physical stability on long-term storage. Form I has the distinct liability that it may change forms upon standing, possibly causing caking of suspensions or poor dissolution from solid dosage forms. These differences demonstrate the obvious advantages of using Form III as an antibiotic drug.

TABLE S

The solubility of the quinolone, Forms I and III, in ethyl acetate at 20° C.

| | Concentration in mg/ml | |
|---|---|---|
| Time (hours) | Form I | Form III |
| 1 | 2.89, 2.78 | 0.06, 0.09 |
| 2 | 2.18, 2.99 | 0.11, 0.11 |
| 4.5 | 3.01, 3.11 | 0.12, 0.12 |
| 18 | 3.02, 3.08 | 0.14, 0.14 |
| 24 | 3.24, 3.32 | 0.15, 0.15 |
| 67.5 | 3.22, 3.24 | 0.14, 0.14 |

The following examples are intended to be illustrative and are not intended to limit the invention in any way.

EXAMPLES

Preparation of Form I

The quinolone (205 g) is dissolved in 4 L of methanol under reflux and clarified by filtration through a glass funnel. The filtrate is allowed to cool to room temperature over 1 h and then cooled to 0° C. for 1 h. The solids formed are collected on a glass funnel and dried in a vacuum oven at 50° C. to constant weight to afford 94 g of crystalline Form I. This material is extensively characterized.

Preparation of Form III

Form III is obtained by dissolving 2.7 g of Form I in 50 ml of hot methanol and clarifying by filtration through a glass funnel. The clear yellow solution is distilled to remove about 25 ml of methanol and 50 ml of ethyl acetate are added slowly during the continued distillation of methanol. After distilling off another 40 ml of solvent, another 50 ml of ethyl acetate are added and distillation continued until the pot temperature had risen to 74° C. The off-white precipitate is filtered hot on a glass funnel, washed with 2×25 ml of ethyl acetate, and dried in a vacuum oven to afford 2.0 g of Form III.

Preparation of the Methanol solvate, Form MS

A methanol solvate is prepared by dissolving 200 mg of the quinolone Form I, in about 8 ml of methanol. The suspension is sealed in a glass vial and heated over a steam bath to achieve complete dissolution. The sample is allowed to cool overnight and crystals are collected by vacuum filtration the following morning. To prevent spontaneous desolvation in the absence of methanol vapor, the inlet to the collection funnel is connected to tubing that drew air through a bubbler flask containing a 50/50 v/v mixture of methanol/butanol. The butanol is added to this mixture to reduce the activity of methanol vapor. About 100 mg of crystals are collected.

XRD patterns of the quinolone, Forms I, II, III, and MS are provided, in tables I, II, III, and IV, below. For these tables * is diffraction peak of the Aluminum sample tray, # indicates the relative intensity for each peak is determined by ratioing its intensity to that of the strongest peak at 17.40 degree angle as 100.

TABLE I

Characteristic XRD Diffraction peaks of Form I.

| Two-Theta Angle (degree) | d-Spacing (Angstrom) | Relative Intensity# (arbitrary) |
|---|---|---|
| 38.40* | 2.342 | 19 |
| 38.20 | 2.354 | 19 |
| 24.35 | 3.652 | 54 |
| 22.75 | 3.906 | 16 |
| 21.70 | 4.092 | 46 |
| 21.45 | 4.139 | 61 |
| 19.45 | 4.560 | 27 |
| 18.90 | 4.692 | 21 |
| 18.05 | 4.911 | 18 |
| 17.40 | 5.093 | 100 |
| 15.25 | 5.805 | 23 |
| 12.05 | 7.339 | 15 |
| 11.95 | 7.400 | 15 |
| 10.65 | 8.300 | 80 |
| 10.35 | 8.540 | 56 |
| 9.65 | 9.158 | 68 |

TABLE II

Characteristic XRD Diffraction peaks of Form II

| Two-Theta Angle (degree) | d-Spacing (Angstrom) | Relative Intensity# (arbitrary) |
|---|---|---|
| 38.40* | 2.342 | 23 |
| 38.15 | 2.357 | 41 |
| 27.55 | 3.235 | 22 |
| 25.50 | 3.490 | 100 |
| 23.50 | 3.783 | 73 |
| 22.35 | 3.975 | 28 |
| 21.75 | 4.083 | 25 |
| 21.35 | 4.158 | 23 |
| 20.15 | 4.403 | 41 |
| 18.70 | 4.741 | 24 |
| 17.45 | 5.078 | 19 |
| 16.00 | 5.535 | 15 |
| 15.50 | 5.712 | 17 |
| 14.70 | 6.021 | 27 |
| 14.35 | 6.167 | 16 |
| 9.30 | 9.502 | 71 |
| 8.75 | 10.098 | 52 |

TABLE III

Characteristic XRD Diffraction peaks of Form III

| Two-Theta Angle (degree) | d-Spacing (Angstrom) | Relative Intensity# (arbitrary) |
|---|---|---|
| 38.40* | 2.342 | 7 |
| 38.20 | 2.354 | 6 |
| 35.25 | 2.544 | 6 |
| 33.65 | 2.661 | 7 |
| 29.85 | 2.991 | 6 |
| 28.15 | 3.167 | 11 |
| 26.35 | 3.380 | 6 |
| 25.90 | 3.437 | 7 |
| 23.95 | 3.713 | 8 |
| 23.40 | 3.799 | 10 |
| 23.10 | 3.847 | 28 |
| 22.45 | 3.957 | 13 |
| 21.50 | 4.130 | 100 |
| 19.75 | 4.492 | 9 |
| 18.65 | 4.754 | 12 |
| 17.80 | 4.979 | 14 |
| 14.40 | 6.146 | 8 |
| 13.90 | 6.366 | 20 |
| 9.80 | 9.0181 | 61 |

TABLE IV

Characteristic XRD Diffraction peaks of Form MS

| Two-Theta Angle (degree) | d-Spacing (Angstrom) | Relative Intensity# (arbitrary) |
|---|---|---|
| 38.40* | 2.342 | 20 |
| 38.10 | 2.360 | 37 |
| 28.75 | 3.103 | 16 |
| 27.95 | 3.190 | 28 |
| 27.45 | 3.247 | 15 |
| 26.55 | 3.355 | 28 |
| 26.45 | 3.367 | 25 |
| 24.70 | 3.602 | 15 |
| 23.60 | 3.767 | 32 |
| 22.60 | 3.931 | 35 |
| 22.45 | 3.957 | 31 |
| 21.05 | 4.217 | 13 |
| 19.85 | 4.469 | 16 |
| 19.50 | 4.549 | 70 |
| 17.85 | 4.965 | 30 |
| 17.40 | 5.093 | 63 |
| 14.25 | 6.210 | 12 |
| 12.85 | 6.884 | 11 |
| 8.70 | 10.156 | 100 |

We claim:

1. The crystal form of [S-(R*,S*)]-1-cyclopropyl-6-fluoro-1,4-dihydro-8-methoxy-7-[3-[1-(methylamino)ethyl] 1-pyrrolidinyl]-4-oxo-3-quinolinecarboxyl acid, having the formula shown below, and having a melting onset range, as determined by Differential Scanning Calorimetry (DSC) between 190–202° C.

2. The compound of claim 1, having a melting onset range, as determined by Differential Scanning Calorimetry (DSC) between 195–201° C.

3. The compound of claim 2, having a melting onset range, as determined by Differential Scanning Calorimetry (DSC) between 198–201° C.

4. The compound of claim 2 having a DSC profile as shown in FIG. 5.

5. The crystal form of [S-(R*,S*)]-1-cyclopropyl-6-fluoro-1,4-dihydro-8-methoxy-7-[3-[1-(methylamino) ethyl]-1-pyrrolidinyl]4-oxo-3-quinolinecarboxyl acid, having the formula shown below, 6. The compound of claim 5, having a melting onset range, as determined by Differential Scanning Calorimetry (DSC) between 190–202° C.

7. The compound of claim 6, having the X-Ray Diffraction pattern shown in FIG. 4.

8. A pharmaceutical composition which comprises the crystal form of the quinolone of claim 5.

* * * * *